United States Patent
Liu et al.

(10) Patent No.: US 10,360,699 B2
(45) Date of Patent: Jul. 23, 2019

(54) CORRECTING COUNT LOSS

(71) Applicant: Shenyang Neusoft Medical Systems Co., Ltd., Shenyang (CN)

(72) Inventors: Shaolian Liu, Shenyang (CN); Jie Chang, Shenyang (CN); Ming Li, Shenyang (CN)

(73) Assignee: Shenyang Neusoft Medical Systems Co., Ltd., Shenyang (CN)

(*) Notice: Subject to any disclaimer, the term of this patent is extended or adjusted under 35 U.S.C. 154(b) by 65 days.

(21) Appl. No.: 15/793,914

(22) Filed: Oct. 25, 2017

(65) Prior Publication Data

US 2018/0114345 A1    Apr. 26, 2018

(30) Foreign Application Priority Data

Oct. 25, 2016    (CN) .......................... 2016 1 0939541

(51) Int. Cl.
| | | |
|---|---|---|
| *G06K 9/00* | (2006.01) | |
| *G06T 11/00* | (2006.01) | |
| *A61B 6/03* | (2006.01) | |

(52) U.S. Cl.
CPC ............. *G06T 11/005* (2013.01); *A61B 6/037* (2013.01); *G06T 2207/10104* (2013.01)

(58) Field of Classification Search
CPC ........... G01N 2015/1062; G01N 15/12; G01N 2015/025; G01N 15/1227; A61B 6/037; G06T 11/005; G06T 2207/10104
USPC ................. 382/131; 250/367, 363.09; 705/2; 324/71.14; 377/11
See application file for complete search history.

(56) References Cited

U.S. PATENT DOCUMENTS

| | | | | |
|---|---|---|---|---|
| 6,744,245 B2 * | 6/2004 | Taylor | .................... | G01N 15/12 324/71.4 |
| 7,129,497 B2 * | 10/2006 | Wollenweber | .......... | G01T 1/171 250/363.09 |
| 10,147,206 B2 * | 12/2018 | Li | .......................... | G06T 11/003 |

FOREIGN PATENT DOCUMENTS

| | | |
|---|---|---|
| CN | 101501526 A | 8/2009 |
| CN | 103315763 A | 9/2013 |
| CN | 103417235 A | 12/2013 |
| CN | 103698024 A | 4/2014 |

(Continued)

OTHER PUBLICATIONS

Zhou, F. et al., "Experimental Study on the Method of Deadtime Correction for HPGe γ Spectrometer System," High Energy Physics and Nuclear Physics, vol. 29, No. 12, Dec. 2005, 4 pages. (Submitted with English Abstract).

(Continued)

*Primary Examiner* — Charlotte M Baker
(74) *Attorney, Agent, or Firm* — McCoy Russell LLP (57) ABSTRACT

Methods for correcting a count loss and PET systems are provided according to examples of the present disclosure. In one aspect, the PET system obtain scanning data of a subject to be detected for which random correction has been performed, obtain a first correction factor corresponding to the true coincidence count according to the single-photon count rates of the two Blocks corresponding to the true coincidence count, obtain a second correction factor corresponding to the true coincidence count according to the system single-photon count rate, and correct the true coincidence count according to the first correction factor and the second correction factor corresponding to the true coincidence count.

14 Claims, 4 Drawing Sheets

(56) References Cited

FOREIGN PATENT DOCUMENTS

| | | |
|---|---|---|
| CN | 105125231 A | 12/2015 |
| CN | 105212954 A | 1/2016 |

OTHER PUBLICATIONS

Liu, L. et al., "Data corrections in positron emission tomography (PET)," Institute of High Energy Physics, Chinese Academy of Sciences, vol. 112, No. 2, Dec. 2, 2007, 7 pages. (Submitted with English Abstract).

State Intellectual Property Office of the People's Republic of China, Office Action and Search Report Issued in Application No. 201610939541.X, dated Mar. 21, 2019, 11 pages. (Submitted with Partial Translation).

* cited by examiner

CORRECTING COUNT LOSS

CROSS REFERENCE TO RELATED APPLICATIONS

This application claims priority to Chinese Patent Application No. 201610939541.X entitled "Method and Apparatus for Correcting Count Loss in PET System," filed on Oct. 25, 2016, the entire contents of which are incorporated herein by reference for all purposes.

TECHNICAL FIELD

The present disclosure relates to correcting a count loss.

BACKGROUND

Positron Emission Tomography (PET) systems have widely applied to medical fields. The PETs can display morphological structures and provide function information about viscera and lesions thereof at a molecular level. The PETs have excellent performance for diagnosing diseases such as tumors, cardiovascular and nervous systems and the like.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

BRIEF DESCRIPTION OF FIGURES

The details of one or more embodiments of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

A PET system can detect rays emitted from a subject and obtain an image reflecting metabolic conditions for different tissues on the subject through reconstruction. Nevertheless, when the system detects these rays, the number of the rays actually received by the system may be different from the number of the rays emitted from the subject due to effect of various factors such as a structure of a detector system, integration time for a crystal, a front-end electronic, and a coincidence determining circuit. Consequently, it is in demand to correct data obtained by PET through scanning. Data correction can include random correction, normalization correction, count loss correction, scattering correction, attenuation correction, etc.

There are some methods of implementing count loss correction, e.g., a measurement method. However, correction accuracy for the method of correcting the count loss above is low, which causes quality of a reconstructed image to be degraded.

A PET system and some terminologies in examples of the present disclosure are described below.

In the PET system, a radionuclide labeled tracer material is injected into a subject, and the radionuclide releases positrons during a decaying process. When a positron annihilates with an adjacent negatron, a positron annihilation event occurs, and a pair of 511 KeV gamma ($\gamma$)-photons opposite in flight directions are generated. The $\gamma$-photons are collected by a detecting apparatus in the PET system. Analysis is performed according to reception information (e.g., a reception time and a reception position) of the $\gamma$-photons.

Figure 1:
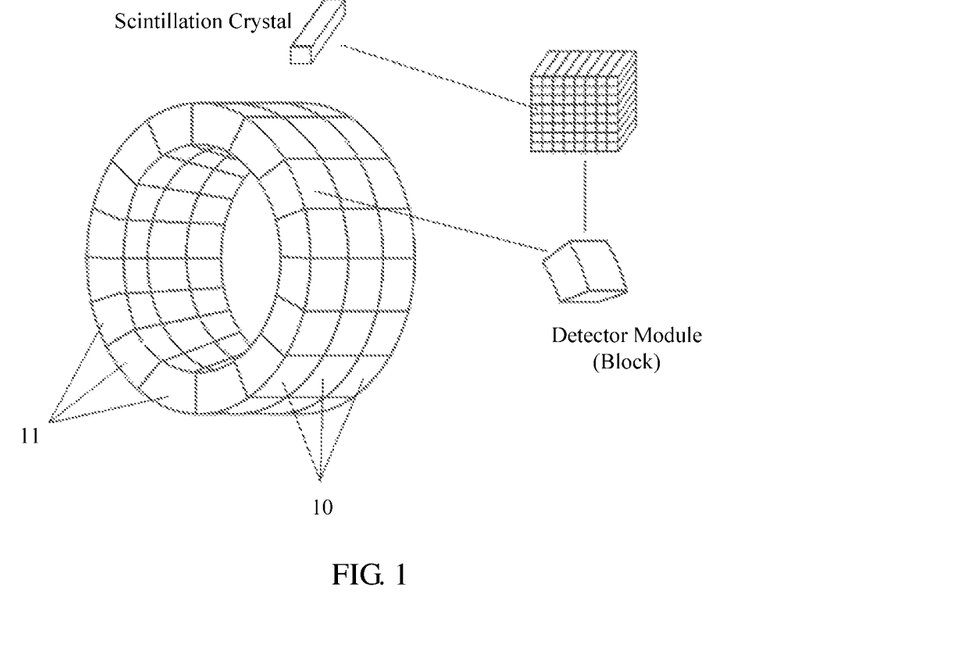
FIG. 1 is a schematic diagram illustrating a detecting apparatus in a PET system according to an example of the present disclosure.

FIG. 1 is a schematic diagram illustrating a detecting apparatus for detecting a $\gamma$-photon pair in a PET system. As shown in FIG. 1, the detecting apparatus in the PET system includes a plurality of detector rings 10 axially arranged. Each detector ring 10 is formed by assembling a plurality of detector modules 11, where a detector module 11 is referred to as "Block" in the present disclosure. Each Block 11 includes a scintillation crystal and a photomultiplier. The scintillation crystal can absorb a $\gamma$-photon and generate a number of visible light photons according to energy of the $\gamma$-photon. The photomultiplier can convert a visible light signal generated by the scintillation crystal into an electric signal for output, for example, a pulse for output.

An event that a $\gamma$-photon detected above is incident into a scintillation crystal is referred to as a "single event". An event that a pair of $\gamma$-photons detected is respectively incident onto a pair of scintillation crystals in a same time window is referred to as a "coincidence event". Coincidence events may be classified into a true coincidence event, a scatter coincidence event, and a random coincidence event. When two $\gamma$-photons detected are from a same positron annihilation event and none of the two $\gamma$-photons have angular deflection, the coincidence event is the true coincidence event. When two $\gamma$-photons detected are from a same positron annihilation event and at least one of the two $\gamma$-photons has the angular deflection, the coincidence event is the scatter coincidence event. When two $\gamma$-photons detected are from different positron annihilation events, the coincidence event is the random coincidence event. Only the true coincidence event contains accurate location information. Data obtained according to the coincidence event is coincidence data.

According to examples of the present disclosure, unless otherwise stated, "single-photon count rate" is a count of single-photons (e.g., γ-photons produced in a positron annihilation event) received in a unit time period during the scanning process. "System single-photon count rate" is a sum of counts of single-photons received by different Blocks on a detection apparatus in the unit time period during the scanning process. "True coincidence count rate" is a true coincidence count rate for which the random correction has been performed, which includes a count of true coincidence events and a count of scatter coincidence events detected in the unit time period during the scanning process. "System true coincidence count rate" is a system true coincidence count rate for which the random correction has been performed, which is a sum of counts of true coincidence events and counts of scatter coincidence events between every two of the Blocks in the unit time period.

Technical solutions of the present disclosure are described below in conjunction with the accompanying drawings and examples.

Figure 2:
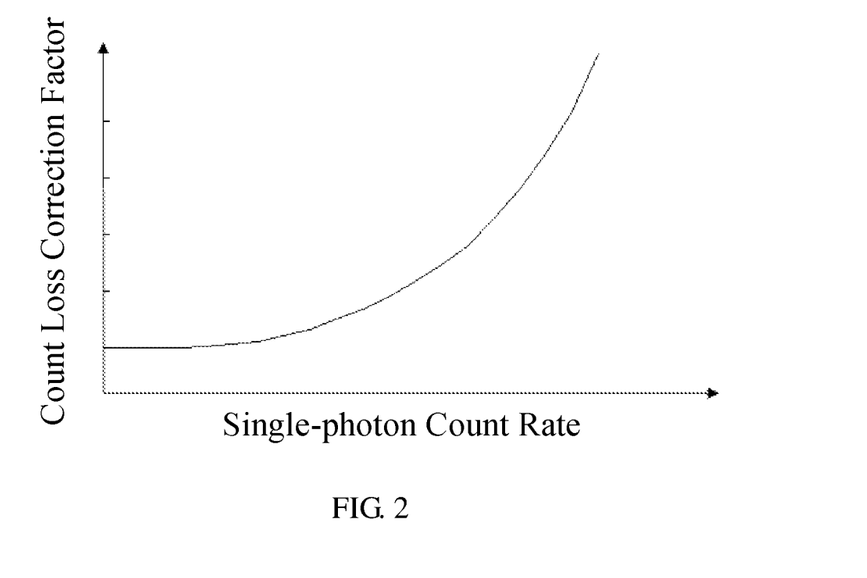
FIG. 2 is a schematic diagram illustrating a functional relationship between single-photon count rate and count loss correction factor according to an example of the present disclosure.

A measurement method can be used for correcting a count loss. According to the measurement method, system single-photon count rates and system true coincidence event count rates for a designated phantom at different pharmaceutical activities are measured, a functional relationship (or a searching table) between the system single-photon count rate and the count loss correction factor, e.g., a functional relationship in FIG. 2, is built according to measurement data. At a clinical scanning stage, the system single-photon count rate actually measured is substituted into the functional relationship above to obtain a correction factor, and the system true coincidence event count rate actually measured is corrected based on the obtained correction factor.

Since the functional relationship is obtained based on the designated phantom which corresponds to a designated single-photon distribution situation, the count loss correction factor obtained by substituting the system single-photon count rate measured at the clinical scanning stage into the functional relationship is a correction factor used under a designated system single-photon distribution situation. However, the phantom used at the clinical scanning stage may not be exactly consistent with the phantom used at the modelling stage, e.g., phantom placement positions and pharmaceutical distributions in the phantom are different from each other, which may cause a single-photon distribution situation at the clinical scanning stage to be different from that at the modelling stage. Accordingly, the correction factor used at the clinical scanning stage may be different from the correction factor calculated through the functional relationship.

According to the methods above for correcting a count loss, the correction factor is obtained directly according to the system single-photon count rate and without regarding single-photon distribution difference, e.g., it may be regarded that single-photon count rates at different Blocks are the same. Thus, in the methods above, coincidence loss conditions are the same accordingly, e.g., loss conditions for coincidence data of different Blocks are the same. Actually, a Block with a high single-photon count rate has a great single-photon loss, and true coincidence count loss related with the block is great accordingly. In contrast, a Block with a low single-photon count rate has a less single-photon loss, and true coincidence count loss related with the block is less accordingly. Thus, a correction deviation may be caused when only the system single-photon count rate is used for correction, which causes that accuracy of a total value of the system true coincidence count for which count loss correction has been performed is degraded. Further, distribution of system true coincidence counts is not accurate, and a quality of a reconstructed image is degraded, which is bad for quantitative analysis.

In examples of the present disclosure, based on a Block structure of a detector, factors for a true coincidence count loss include a count of single-photons lost for a Block, e.g., a single-photon count loss at each Block causes the true coincidence count loss, and a count of received single-photons. For the count of the received single-photons, the true coincidence count is a coincidence count obtained based on single-photons received by the system. When the system single-photon count rate is high, a loss of the true coincidence count may be caused due to factors such as multiple coincidences (e.g. a same photon satisfies coincidence events respectively with a previous photon and a latter photon). According to the two factors above, a functional relationship between single-photon count rate and single-photon count rate loss correction factor of Block and a functional relationship between system single-photon count rate and coincidence loss correction factor are respectively built. The two functional relationships are used to perform count loss correction in a way that the effect of single-photon distribution difference on the true coincidence count rate can be eliminated.

A method of correcting a count loss in a PET system is provided according to an example of the present disclosure. The method includes a modelling stage and a clinical scanning stage. The modelling stage includes building a functional relationship between single-photon count rate and single-photon count rate loss correction factor of Block and a functional relationship between system single-photon count rate and coincidence loss correction factor. The clinical scanning stage includes performing correction for clinical scanning data based on two models built at the modelling stage, and obtaining a PET image according to the corrected clinical scanning data. In description below, it is described how the two models above are built at the modelling stage and how count correction is performed based on the two obtained models.

I. Modelling Stage

In a first step, scanning is performed for a phantom injected with a radiopharmaceutical over a plurality of time periods, and a pharmaceutical activity $a_i$, an actual system single-photon count rate $S_i$, an actual single-photon count rate $s_{ji}$ of each Block, an actual true coincidence count rate $T_{j_1 j_2 i}$ of every two Blocks and an actual system true coincidence count Ti in a time period i are determined, where i is a number for a time period, j is a number for a Block; $j_1$ and $j_2$ express numbers for two different Blocks, a value range of j1 is 1 to K, a value range of j2 is 1 to K, and K expresses the number of Blocks.

In an example, the phantom (e.g., cylindrical phantom) injected with the radiopharmaceutical can uniformly emit rays in the PET system, and an initial activity of the radiopharmaceutical exceeds an activity desired when performing scanning for a patient, such as 50 (mCi). The PET system performs scanning over a plurality of time periods. Since the pharmaceutical decays over time, its activity may become lower and lower. Lower an activity, less loss of counts (including a single-photon count and a true coincidence count). Consequently, almost no count loss occurs in last few scanning time periods by controlling the pharmaceutical activity.

A mean pharmaceutical activity $a_i$ in the time period i is calculated according to pharmaceutical decay. The single-photon count for each Block, the system single-photon count, the true coincidence count between every two Blocks and the system true coincidence count in the time period i are respectively divided by a length of the time period i to obtain $s_{ji}$, $S_i$, $T_{j_1 j_2 i}$ and $T_i$.

In a second step, a single-photon count loss correction factor for each Block is calculated based on the data obtained in the first step, and a functional relationship between the single-photon count rate and the single-photon count loss correction factor for each Block is built.

For each Block, an implementing process includes procedures as follows.

In some time periods without count loss under a minimum activity, based on a principle that the single-photon count rate is increased in direct proportion to increase of activity when there is no count loss, a ratio $\lambda_j$ of a theoretical single-photon count rate of the Block to an activity in the condition without count loss is obtained according to pharmaceutical activities and actual single-photon count rates of the Block in the time periods under the minimum activity, such as $a_i$ and $s_{ji}$ in M time periods without count loss:

$$\lambda_j = [\Sigma(s_{ji}/a_i)]/M \qquad \text{Formula (1)}$$

$$\text{or } \lambda_j = (\Sigma s_{ji})/(\Sigma a_i) \qquad \text{Formula (2)}$$

It is assumed that a scan lasts for N time periods in total, which are sequentially numbered as 1, 2, ... N−1, and N, and there is no count loss for the Block in last M time periods, the above Formula (1) and Formula (2) may further be expressed as:

$$\lambda_j = [\Sigma_{i=N-m+1}^{N}(s_{ji}/a_i)]/M \qquad \text{Formula (3)}$$

$$\lambda_j = (\Sigma_{i=N-m+1}^{N} s_{ji})/(\Sigma_{i=N-m+1}^{N} a_i) \qquad \text{Formula (4)}$$

A theoretical single-photon count rate $\bar{s}_{ji}$ of the Block in each time period i is calculated according to the above obtained ratio $\lambda_j$:

$$\bar{s}_{ji} = \lambda_j a_i \qquad \text{Formula (5)}$$

The theoretical single-photon count rate $\bar{s}_{ji}$ is a single-photon count rate in a case without single-photon loss.

The $\bar{s}_{ji}$ is divided by an single-photon count rate $s_{ji}$ to obtain a single-photon count loss correction factor $\eta_{ji}$ for the Block in the time period i:

$$\eta_{ji} = \bar{s}_{ji}/s_{ji} \qquad \text{Formula (6)}$$

The functional relationship $\eta_j = f_j(s)$ between the single-photon count rate and the single-photon count loss correction factor for the Block can be built according to the above obtained data sequences $n_{ji}$ and $s_{ji}$.

In examples of the present disclosure, the functional relationship may further be expressed by a single-photon count loss correction model.

The function $f_j(s)$ may be a polynomial function or a piecewise function.

When $f_j(s)$ is the polynomial function, it may be expressed in a form as follows:

$$f_j(s) = \Sigma_{k=0}^{n} = a_k s^k \qquad \text{Formula (7)}$$

In the polynomial function, s is the single-photon count rate (or the single-photon count) of the Block; n is a dimension of a preset polynomial; and $a_k$ is a polynomial coefficient, which is obtained by polynomial fitting for the data sequences; $\eta_{ji}$ and $s_{ji}$.

When $f_j(s)$ is the piecewise function, it may be expressed in the following form:

$$f_j(s) = \begin{cases} \eta_{ji}, & s = s_{ji} \\ \text{obtained by interpolation,} & s = \text{another value} \end{cases} \qquad \text{Formula (8)}$$

In the piecewise function, s is the single-photon count rate (or the single-photon count) of the Block; $\eta_{ji}$ and $s_{ji}$ in Formula (8) are the data sequences above. According to the interpolation method, another value is obtained by linear interpolation or another interpolation method based on $\eta_{ji}$ corresponding to $s_{ji}$ near s.

In a third step, an actual true coincidence count rate $T_{j_1 j_2 i}$ for Blocks is corrected according to the single-photon count loss correction factor $\eta_{ji}$ for each of the Blocks in each time period obtained in the second step in a way that the effect of a single-photon count loss can be eliminated.

An implementation process includes procedure as follows.

A single-photon count loss correction factor $\eta_{ji}$ for each Block in each time period i is obtained according to Formulas (1)-(6) in the second step. Since a single-photon count loss may cause a true coincidence count loss, a correction factor $\xi_{j_1 j_2 i}$ for eliminating impact of the single-photon count loss on the true coincidence count between two different Blocks is $\xi_{j_1 j_2 i}$:

$$\xi_{j_1 j_2 i} = \eta_{j_1 i} \eta_{j_2 i} \qquad \text{Formula (9)}$$

In Formula (9), $j_1$ and $j_2$ may be the same as described above, e.g., expressing numbers for the two different Blocks; $\eta_{j_1 i}$ expresses a single-photon count loss correction factor corresponding to Block $j_1$, and $\eta_{j_2 i}$ expresses a single-photon count loss correction factor corresponding to Block $j_2$.

When the effect of the single-photon count loss is eliminated, a true coincidence count rate $\bar{T}_{j_1 j_2 i}$ between the two different Blocks in each time period is:

$$\bar{T}_{j_1 j_2 i} = \eta_{j_1 i} \eta_{j_2 i} T_{j_1 j_2 i} \qquad \text{Formula (10)}$$

Based on the true coincidence count rate $\bar{T}_{j_1 j_2 i}$ obtained according to Formula (10), the effect of the single-photon count loss can be eliminated. The system true coincidence count rate $\bar{T}_i$ in each period time for which the effect of the single-photon count loss has been eliminated is obtained by obtaining a sum of the true coincidence count rate $\bar{T}_{j_1 j_2 i}$ of every two Blocks in the time period.

In a fourth step, in some time periods without count loss under a minimum activity, based on a principle that the single-photon count rate is increased in direct proportion to increase of activity when there is no count loss, a ratio $\alpha$ of a true coincidence count rate to a pharmaceutical activity in the condition without count loss is obtained based on actual system true coincidence count rates $\bar{T}_i$ and a pharmaceutical activities $a_i$ in some time periods under the minimum activity, such as $\bar{T}_i$ and $a_i$ in M time periods without count loss.

$$\alpha = [\Sigma(\bar{T}_i/a_i)]/M \qquad \text{Formula (11)}$$

$$\text{or } \alpha = (\Sigma \bar{T}_i)/(\Sigma a_i) \qquad \text{Formula (12)}$$

It is assumed that a scan lasts for N periods of time in total, which are sequentially numbered as 1, 2, ... N−1, and N, and the system has no count loss in last M time periods, the above Formula (11) and Formula (12) may further be expressed as:

$$\alpha = [\Sigma_{i=N-M+1}^{N}((T_i/a_i))]/M \quad \text{Formula (13)}$$

$$\text{or } \alpha = [_{i=N-M+1}^{N}((T_i/a_i))]/M \quad \text{Formula (14)}$$

A theoretical system true coincidence count rate $\hat{T}_i$ in each time period i may be calculated according to the above obtained ratio $\alpha$:

$$\hat{T}_i = \alpha a_i \quad \text{Formula (15)}$$

In a fifth step, a single-photon count loss correction factor for each Block is calculated according to the data obtained in the third step and the fourth step, and a functional relationship between the system single-photon count rate and the coincidence loss correction factor is built.

In an example, a coincidence loss correction factor $\omega_i$ in each time period i for every two Blocks is obtained by dividing the theoretical system true coincidence count rate $\hat{T}_i$ obtained in the fourth step by the $T_i$ obtained in the third step to obtain:

$$\omega_i = \hat{T}_i/T_i \quad \text{Formula (16)}$$

The functional relationship $\omega = g(S)$ between the system single-photon count rate and the coincidence loss correction factor is built according to the obtained data sequence $\omega_i$ and the corresponding system single-photon count rate $S_i$.

In examples of the present disclosure, the functional relationship may be demonstrated by a true coincidence count loss correction model.

The function g(S) may be a polynomial function or a piecewise function.

When g(S) is the polynomial function, it may be expressed in the following form:

$$g(S) = E_{k=0}^{l} b_k S^k \quad \text{Formula (17)}$$

In the polynomial function, S is the system single-photon count rate (or the system single-photon count); l is a dimension of the preset polynomial; and $b_k$ is a polynomial coefficient, which is obtained by polynomial fitting based on the data sequences $\omega_i$ and $S_i$.

When g(S) is the piecewise function, it may be expressed in the following form:

$$g(S) = \begin{cases} \omega_i, & S = S_i \\ \text{obtained by interpolation,} & S = \text{anther value} \end{cases} \quad \text{Formula (18)}$$

In the piecewise function, S is the system single-photon count rate (or the system single-photon count); $\omega_I$ and $S_I$ in Formula (18) are the data sequence above. In an interpolation method, the g(S) when S is equal to another value is obtained by linear interpolation or another interpolation methods based on $\omega_i$ corresponding to $S_i$ near S.

II. Clinical Scanning Stage

At this stage, PET scanning is performed for a subject to be detected to obtain scanning data, where the scanning data includes a single-photon count rate of each Block, a system single-photon count rate, and a true coincidence count between every two Blocks. The true coincidence count between every two Blocks in the original scanning data includes a count of true coincidence events for the two Blocks, a count of scatter coincidence events for the Blocks and a count of random coincidence events for the two Blocks.

The PET system performs random correction for the scanning data to delete a count of random coincidence events in the true coincidence count. After random correction is performed, the true coincidence count between every two Blocks includes the count of true coincidence events for the two Blocks and the count of scatter coincidence events for the two Blocks.

According to an example of the present disclosure, count loss correction is performed for the scanning data after the random correction is performed, e.g., correction is performed for the true coincidence count between every two Blocks.

Figure 3:
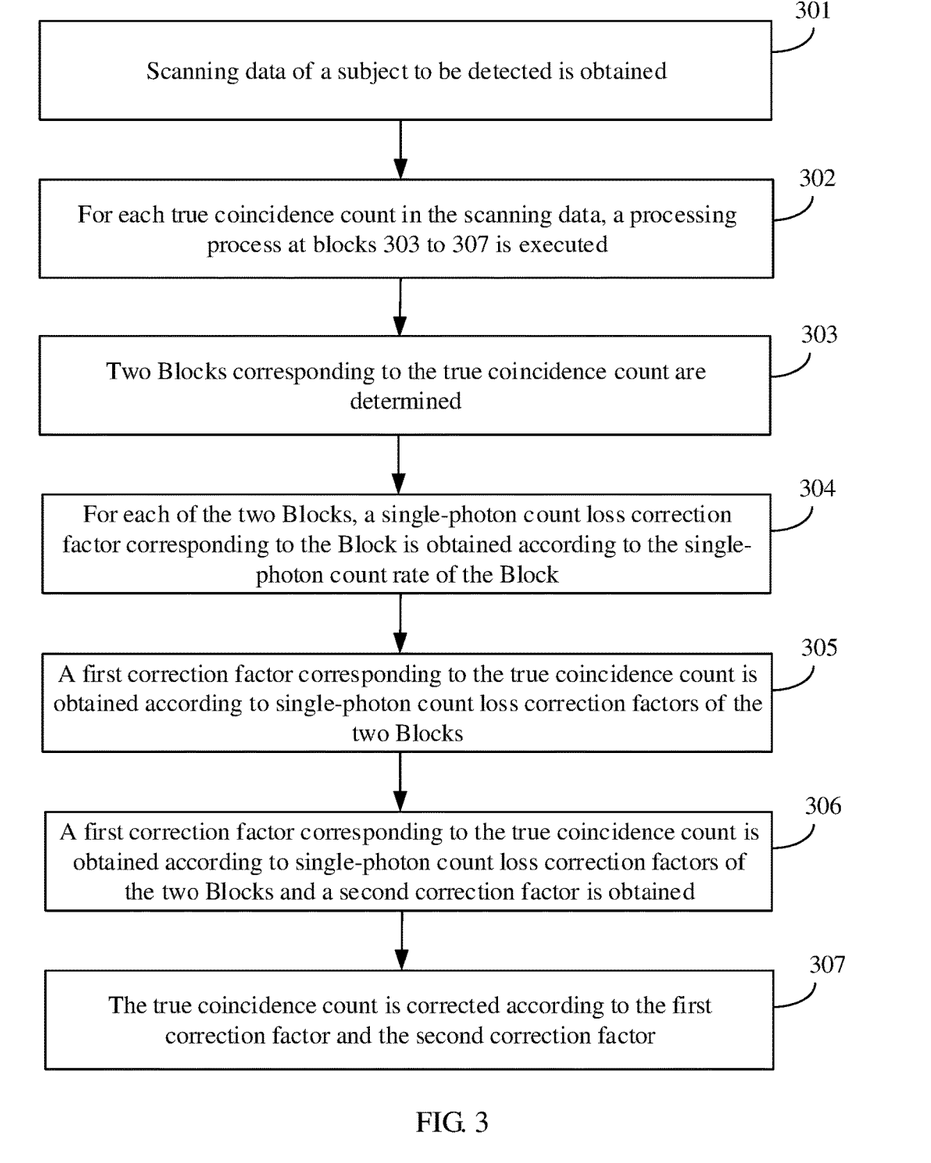
FIG. 3 is a flowchart illustrating a method of correcting a count loss according to an example of the present disclosure.

FIG. 3 is a flowchart illustrating a method of correcting a count loss according to an example of the present disclosure. The method may apply to a PET system to correct a true coincidence count between every two Blocks. The method includes procedures as follows.

At block 301, scanning data of a subject to be detected is obtained, where random correction has been performed for the scanning data, and the scanning data includes a single-photon count rate for each Block, a true coincidence count between every two Blocks, and a system single-photon count rate.

The system single-photon count rate is a sum of single-photon count rates of different Blocks in the PET system.

At block 302, for each true coincidence count in the scanning data, a processing process at blocks 303 to 307 is executed.

At block 303, two Blocks corresponding to the true coincidence count are determined.

For example, when determining a true coincidence count, the PET system may record the numbers for two Blocks receiving γ-photons every time when a true coincidence event occurs in a way that it can be easily determined to which two Blocks the true coincidence count corresponds.

At block 304, for each of the two Blocks, a single-photon count loss correction factor corresponding to the Block is obtained according to the single-photon count rate of the Block.

Figure 4:
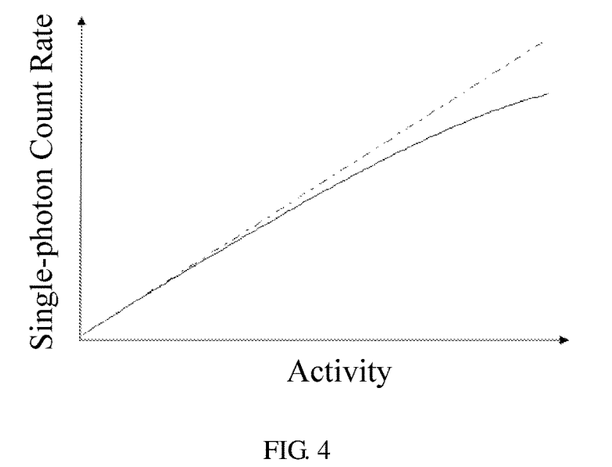
FIG. 4 is a schematic diagram illustrating a changing curve of single-photon count rate and pharmaceutical activity according to an example of the present disclosure.

As shown in FIG. 4, a single-photon count rate of a detector is expressed to be a linear rising region and a nonlinear region along with change of the pharmaceutical activity. The single-photon count loss correction factor herein is used for correcting the effect of the pharmaceutical activity on the single-photon count.

In an example, the single-photon count loss correction factor $\eta_j$ may be obtained by substituting the single-photon count rate of the Block in the scanning process into a functional relationship $\eta_j = f_j(s)$ between single-photon count rate and single-photon count loss correction factor of Block obtained at the modelling stage, i.e., Formula (7) or Formula (8) above.

At block 305, a first correction factor corresponding to the true coincidence count is obtained according to single-photon count loss correction factors of the two Blocks.

The first correction factor may be used for correcting the effect of the single-photon count losses of the two blocks on the true coincidence count.

In an example, the first correction factor may be obtained by multiplying the single-photon count loss correction factors of the two Blocks.

For example, when the true coincidence count between Block 1 and Block 2 is to be corrected, the first correction factor herein is $\eta_1 \eta_2$.

At block 306, a second correction factor corresponding to the true coincidence count is obtained according to the system single-photon count rate in the scanning data.

Since the true coincidence count is a coincidence count of single-photons received by the system. When a system single-photon count rate is high, a loss of the true coincidence count may be caused due to factors such as multiple coincidences. The second correction factor is used for correcting the effect of the system single-photon count on the true coincidence count.

In an example, the second correction factor co is obtained by substituting the system single-photon count rate in the scanning process into the functional relationship $\omega=g(S)$ of system single-photon count rate and coincidence loss correction factor obtained at the modelling stage, i.e., Formula (17) or Formula (18) above.

At block 307, the true coincidence count is corrected according to the first correction factor and the second correction factor.

In an example, the true coincidence count may be multiplied by the first correction factor and the second correction factor to obtain a product as the corrected true coincidence count.

For example, when the true coincidence count $T_{12}$ between Block 1 and Block 2 is to be corrected, the corrected true coincidence count may be expressed as $\eta_1\eta_2\omega T_{12}$, where $\eta_1\eta_2$ represents the first correction factor and co represents the second correction factor.

According to blocks 301 to 307 above, the true coincidence count for which count loss correction is performed may be obtained. Corrections such as the normalization correction (to correct effect of factors produced by efficiency of the detector and a geometric structure of the detector), the scatter correction (to delete a count of scatter events from the true coincidence count) and the decay correction (to compensate true coincidence events lost when $\gamma$ rays pass through a scanned subject) may be performed for the true coincidence count. Based on the true coincidence count obtained through the corrections above, image reconstruction is performed, and a PET reconstructed image of the subject (e.g., a patient) can be obtained accordingly.

According to methods of correcting a count loss in the examples above of the present disclosure, the factors which affect the true coincidence count rate loss includes the effect of a single-photon count lost for a Block on the true coincidence count rate loss and the effect of a count of received single-photons on the true coincidence count rate loss according to the block structure of the detector. The functional relationship between single-photon count rate and single-photon count rate loss correction factor of Block and the functional relationship of system single-photon count rate and coincidence loss correction factor are built. The count loss correction is performed based on the two functional relationships. Thus, effect of single-photon distribution difference on the count loss is eliminated, and accuracy of a total value of corrected true coincidence counts can be improved. Further, accuracy of coincidence data distribution can be improved, quality of the reconstructed image and accuracy of quantitative analysis can be improved.

Methods according to the present disclosure are described above. Devices according to the present disclosure are described below.

A PET (or a PET/CT) scanning device may include a plurality of components such as a scanning gantry, an examination bed, a computer system, an operating console and the like, which is also a PET system. Detector rings for scanning are installed inside the scanning gantry. The methods of correcting a count loss in a PET system provided according to examples of the present disclosure is used in a data processing stage after the scanning data is collected, which can be executed by such as data processing software installed in a computer system.

Figure 5:
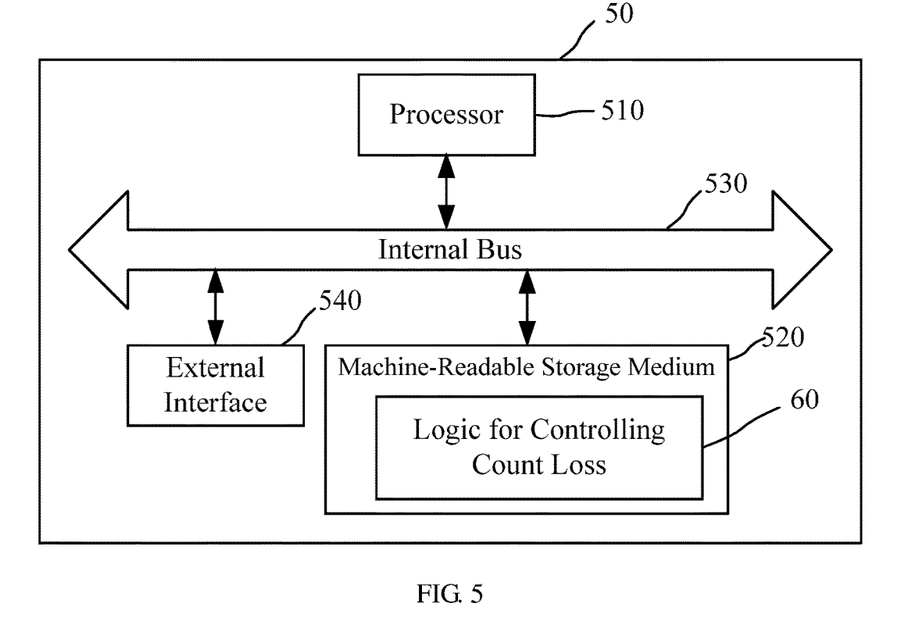
FIG. 5 is a schematic diagram illustrating a structure of a control device according to an example of the present disclosure.

FIG. 5 schematically illustrates a hardware structure diagram of a control device 50 in the PET system, which is provided by an example of the present disclosure. The control device 50 may include a processor 510 and a machine-readable storage medium 520 storing machine executable instructions. The processor 510 may communicate with the machine-readable storage medium 520 via an internal bus 530, and execute the method described above by reading and executing the machine executable instructions corresponding to a packet transmitting control logic 60 in the machine-readable storage medium 520. The control device 50 may further include an external interface 540 to communicate with another device or component.

As used herein, the machine-readable storage medium 520 may be any electronic, magnetic, optical, or other physical storage apparatus to contain or store information such as executable instructions, data, and the like. For example, any machine-readable storage medium described herein may be any of Random Access Memory (RAM), volatile memory, non-volatile memory, flash memory, a storage drive (e.g., a hard drive), a solid state drive, any type of storage disc (e.g., a compact disc, a DVD, etc.), and the like, or a combination thereof.

Figure 6:
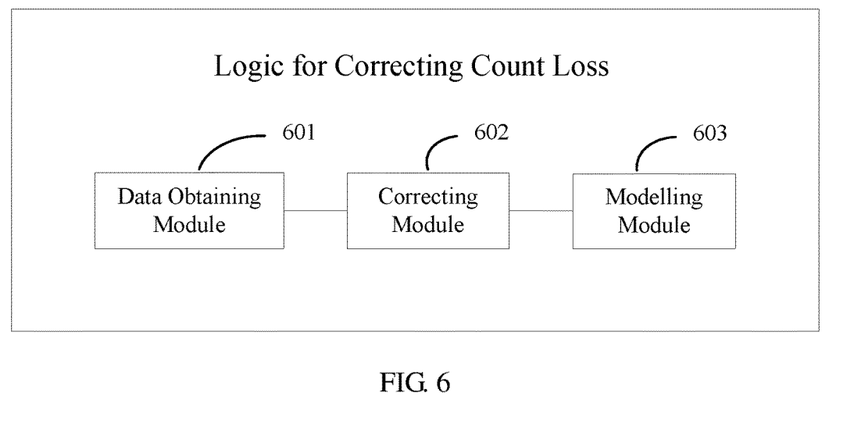
FIG. 6 is a schematic diagram illustrating a structure of logic for correcting a count loss in a PET system according to an example of the present disclosure.

As shown in FIG. 6, functionally divided, the logic 60 for correcting a count loss above may include modules as follows.

A data obtaining module 601 is configured to obtain scanning data of a subject to be detected for which random correction has been performed, wherein the scanning data comprises a single-photon count rate of each of Blocks in the PET system, a true coincidence count between every two of the Blocks and a system single-photon count rate, the system single-photon count rate is a sum of single-photon count rates of the Blocks in the PET system.

A correcting module 602 is configured to obtain a first correction factor corresponding to the true coincidence count according to the single-photon count rates of the two Blocks corresponding to the true coincidence count, wherein the first correction factor is used for correcting an effect of single-photon count losses for the two Blocks corresponding to the true coincidence count on the true coincidence count, obtain a second correction factor corresponding to the true coincidence count according to the system single-photon count rate, wherein the second correction factor is used for correcting an effect of the system single-photon count rate on the true coincidence count; and correct the true coincidence count according to the first correction factor and the second correction factor corresponding to the true coincidence count.

In an example, the correcting module 602 is configured to obtain a single-photon count loss correction factor corresponding to each of the two Blocks according to the single-photon count rate of the Block corresponding to the true coincidence count, obtain the first correction factor corresponding to the true coincidence count according to single-photon count loss correction factors for the two Blocks corresponding to the true coincidence count.

In an example, the correcting module 602 is configured to multiply the single-photon count loss correction factors for the two Blocks to obtain the first correction factor corresponding to the true coincidence count.

In an example, the correcting module 602 is configured to multiply the first correction factor, the second correction factor and the true coincidence count to obtain a product as a corrected true coincidence count.

In an example, the correcting module 602 is configured to obtain a pre-built single-photon count loss correction model for the block, substitute the single-photon count rate of the Block into the single-photon count loss correction model for the block to obtain the single-photon count loss correction factor corresponding to the Block.

In an example, the logic 60 further includes a modelling module 603.

The modelling module 603 is configured to:
a. obtain a single-photon count loss correction factor $\eta_{ji}$ and a corresponding actual single-photon count rate $s_{ji}$ of the Block in each of time periods when scanning a phantom injected with a radiopharmaceutical over the time periods;
b. build the single-photon count loss correction model for the block according to the single-photon count loss correction factor $\eta_{ji}$ and the actual single-photon count rate $s_{ji}$ of the Block in the time period.

In an example, the correcting module 602 is configured to obtain a pre-built true coincidence count loss correction model, substitute the system single-photon count rate into the true coincidence count loss correction model to obtain the second correction factor corresponding to the true coincidence count.

The processor is caused by the machine-executable instructions further to:
determine an actual system single-photon count rate $S_i$, an actual true coincidence count rate between every two Blocks and an actual system true coincidence count rate $T_i$ in each time period i when scanning a phantom injected with a radiopharmaceutical over a plurality of time periods, obtaining, by the PET system, a single-photon count loss correction factor $\eta_{ji}$ for each Block j in the time period i;
multiply single-photon count loss correction factors for the two Blocks in the time period to obtain a product, multiplying, by the PET system, the obtained product by the actual true coincidence count rate for the two Blocks in the time period to obtain the true coincidence count rate for the two Blocks in the time period, wherein the effect of the single-photon count loss has been eliminated for the obtained true coincidence count rate;
obtain a sum of the true coincidence count rates for every two Blocks in each time period to obtain a system true coincidence count rate $\overline{T}_i$ in each time period, wherein the effect of the single-photon count losses has been eliminated for the system true coincidence count rate $\overline{T}_i$;
calculate a ratio $\alpha=[\Sigma(\overline{T}_i/a_i)]/M$ or $\alpha=(\Sigma\ \overline{T}_i)/(\Sigma\ a_i)$ of a theoretical true coincidence count rate to a pharmaceutical activity in a condition that there is no true coincidence count loss according to the actual system true coincidence count rate $\overline{T}_i$ and the pharmaceutical activity $a_i$ in each of M time periods when there is no single-photon count loss;
calculating the theoretical true coincidence count rate $\hat{T}_i=\alpha a_i$ in each time period according to the ratio $\alpha$;
dividing the theoretical true coincidence count rate $\hat{T}_i$ by $T_i$ to obtain a coincidence loss correction factor $\omega_i=\hat{T}_i/T_i$ for every two Blocks in each time period;
building the true coincidence count loss correction model according to $\omega_i$ and the actual system single-photon count rate $S_i$.

In an example, the modelling module 603 is configured to:
determining, by the PET system, a pharmaceutical activity $a_i$ in each of time periods and an actual single-photon count rate $s_{ji}$ for each Block in each of the time periods when scanning a phantom injected with a pharmaceutical over the time periods, wherein i is a number for time period, and j is a number for Block;
calculating, by the PET system, a ratio $\lambda_j$ of a theoretical single-photon count rate of each of the Blocks to a pharmaceutical activity in a condition that there is no single-photon count loss according to the actual single-photon count rate $s_{ji}$ for the Block and the pharmaceutical activities $a_i$ in each of M time periods when there is no single-photon count loss, wherein $\lambda_j=[\Sigma(s_{ji}/a_i)]/M$ or $\lambda_j=(\Sigma\ s_{ji})/(\Sigma\ a_i)$;
calculating, by the PET system, the theoretical single-photon count rate $\overline{s}_{ji}=\lambda_j a_i$ for each of the Blocks in each time period according to the ratio $\lambda_j$;
dividing, by the PET system, $\overline{s}_{ji}$ by the actual single-photon count rate $s_{ji}$ to obtain the single-photon count loss correction factor $\eta_{ji}=\overline{s}_{ji}/s_{ji}$ for each of the Block in each time period.

Since the apparatus embodiments substantially correspond to the method embodiments, a reference may be made to part of the descriptions of the method embodiments for the related part. The apparatus embodiments described above are merely illustrative, where the units described as separate members may be or not be physically separated, and the members displayed as units may be or not be physical units, i.e., may be located in one place, or may be distributed to a plurality of network units. Part or all of the modules may be selected according to actual requirements to implement the objectives of the solutions in the embodiments. Those of ordinary skill in the art may understand and carry out them without creative work.

Example embodiments will be described in detail herein with the examples thereof expressed in the drawings. When the following descriptions involve the drawings, like numerals in different drawings represent like or similar elements unless stated otherwise. The implementations described in the following example embodiments do not represent all implementations consistent with the present disclosure. On the contrary, they are examples of an apparatus and a method consistent with some aspects of the present disclosure described in detail in the appended claims.

The terminology used in the present disclosure is for the purpose of describing a particular example only, and is not intended to be limiting of the present disclosure. The singular forms such as "a", "said", and "the" used in the present disclosure and the appended claims are also intended to include multiple, unless the context clearly indicates otherwise. It is also to be understood that the term "and/or" as used herein refers to any or all possible combinations that include one or more associated listed items.

It is to be understood that although different information may be described using the terms such as first, second, third, etc. in the present disclosure, these information should not be limited to these terms. These terms are used only to distinguish the same type of information from each other. For example, the first information may also be referred to as the second information without departing from the scope of the present disclosure, and similarly, the second information may also be referred to as the first information. Depending on the context, the word "if" as used herein may be interpreted as "when" or "as" or "determining in response to".

The foregoing disclosure is merely illustrative of example embodiments of the disclosure but not intended to limit the disclosure, and any modifications, equivalent substitutions, adaptations thereof made without departing from the spirit and scope of the disclosure shall be encompassed in the claimed scope of the appended claims.

The invention claimed is:

1. A method of correcting a count loss, comprising:
obtaining, by a Positron Emission Tomography (PET) system, scanning data of a subject to be detected for which random correction has been performed, wherein the scanning data comprises a single-photon count rate of each of a plurality of Blocks in the PET system, a true coincidence count between every two of the Blocks, and a system single-photon count rate, where the system single-photon count rate is a sum of single-photon count rates of the Blocks in the PET system;
determining, by the PET system, a first correction factor corresponding to the true coincidence count according to the single-photon count rates of the two Blocks corresponding to the true coincidence count, wherein the first correction factor is used for correcting an effect of single-photon count losses for the two Blocks corresponding to the true coincidence count on the true coincidence count;
determining, by the PET system, a second correction factor corresponding to the true coincidence count according to the system single-photon count rate, wherein the second correction factor is used for correcting an effect of the system single-photon count rate on the true coincidence count; and
correcting, by the PET system, the true coincidence count according to the first correction factor and the second correction factor corresponding to the true coincidence count.

2. The method of claim 1, wherein determining the first correction factor corresponding to the true coincidence count according to the single-photon count rates of the two Blocks corresponding to the true coincidence count comprises:
obtaining, by the PET system, a single-photon count loss correction factor corresponding to each of the two Blocks according to the single-photon count rate of the Block corresponding to the true coincidence count; and
determining, by the PET system, the first correction factor corresponding to the true coincidence count according to single-photon count loss correction factors for the two Blocks corresponding to the true coincidence count.

3. The method of claim 2, wherein determining the first correction factor corresponding to the true coincidence count according to the single-photon count loss correction factors for the two Blocks corresponding to the true coincidence count further comprises:
multiplying, by the PET system, the single-photon count loss correction factors for the two Blocks to obtain the first correction factor corresponding to the true coincidence count.

4. The method of claim 2, wherein obtaining the single-photon count loss correction factor corresponding to the Block according to the single-photon count rate of the Block comprises:
obtaining, by the PET system, a pre-built single-photon count loss correction model for the Block;
substituting, by the PET system, the single-photon count rate of the Block into the single-photon count loss correction model for the block to obtain the single-photon count loss correction factor corresponding to the Block,
wherein a process of building the single-photon count loss correction model for each of the two blocks comprises:
obtaining, by the PET system, a single-photon count loss correction factor $\eta_{ji}$ and a corresponding actual single-photon count rate $s_{ji}$ of the Block in each of a plurality of time periods when scanning a phantom injected with a radiopharmaceutical over the plurality of the time periods;
building, by the PET system, the single-photon count loss correction model for the block according to the single-photon count loss correction factor $\eta_{ji}$ and the actual single-photon count rate $s_{ji}$ of the Block in the plurality of the time periods.

5. The method of claim 4, wherein obtaining the single-photon count loss correction factor $\eta_{ji}$ for each Block in each of the plurality of the time periods comprises:
determining, by the PET system, a pharmaceutical activity $\alpha_i$ in each of the plurality of the time periods and an actual single-photon count rate $s_{ji}$ for each Block in each of the plurality of the time periods when scanning a phantom injected with a pharmaceutical over the plurality of the time periods, wherein i is a time period, and j is a Block;
calculating, by the PET system, a ratio $\lambda_j$ of a theoretical single-photon count rate of each of the Blocks to a pharmaceutical activity in a condition that there is no single-photon count loss according to the actual single-photon count rate $s_{ji}$ for the Block and the pharmaceutical activities $a_i$ in each of M time periods when there is no single-photon count loss, wherein $\lambda_j=[\Sigma(s_{ji}/a_i)]/M$ or $\lambda_j=(\Sigma\ s_{ji})/(\Sigma\ \alpha_i)$;
calculating, by the PET system, the theoretical single-photon count rate $\bar{s}_{ji}=\lambda_j\alpha_i$ for each of the Blocks in each of M time periods according to the ratio $\lambda_j$;
dividing, by the PET system, $\bar{s}_{ji}$ by the actual single-photon count rate $s_{ji}$ to obtain the single-photon count loss correction factor $\eta_{ji}=\bar{s}_{ji}/s_{ji}$ for each of the Blocks in each of M time periods.

6. The method of claim 1, wherein correcting the true coincidence count according to the first correction factor and the second correction factor corresponding to the true coincidence count comprises:
multiplying, by the PET system, the first correction factor, the second correction factor, and the true coincidence count to obtain a product as a corrected true coincidence count.

7. The method of claim 1, wherein determining the second correction factor corresponding to the true coincidence count according to the system single-photon count rate comprises:
obtaining, by the PET system, a pre-built true coincidence count loss correction model;
substituting, by the PET system, the system single-photon count rate into the true coincidence count loss correction model to obtain the second correction factor corresponding to the true coincidence count,
wherein a process of building the true coincidence count loss correction model comprises:
determining, by the PET system, an actual system single-photon count rate $S_i$, an actual true coincidence count rate between every two Blocks, and an actual system true coincidence count rate $T_i$ in each time period i when scanning a phantom injected with a radiopharmaceutical over a plurality of time periods, obtaining, by the PET system, a single-photon count loss correction factor $\eta_{ji}$ for each Block j in the time period i;

multiplying, by the PET system, single-photon count loss correction factors for the two Blocks in the time period to obtain a product, multiplying, by the PET system, the obtained product by the actual true coincidence count rate for the two Blocks in the time period to obtain the true coincidence count rate for the two Blocks in the time period, wherein the effect of the single-photon count loss has been eliminated for the obtained true coincidence count rate;

obtaining, by the PET system, a sum of the true coincidence count rates for every two Blocks in each time period to obtain a system true coincidence count rate $T_i$ in each time period, wherein the effect of the single-photon count losses has been eliminated for the system true coincidence count rate $T_i$;

calculating, by the PET system, a ratio $\alpha = [\Sigma(T_i/a_i)]/M$ or $\alpha = (\Sigma T_i)/(\Sigma a_i)$ of a theoretical true coincidence count rate to a pharmaceutical activity in a condition that there is no true coincidence count loss according to the actual system true coincidence count rate $T_i$ and the pharmaceutical activity $a_i$ in each of M time periods when there is no single-photon count loss;

calculating, by the PET system, the theoretical true coincidence count rate $\hat{T}_i = \alpha a_i$ in each time period according to the ratio $\alpha$;

dividing, by the PET system, the theoretical true coincidence count rate $\hat{T}_i$ by $T_i$ to obtain a coincidence loss correction factor $\omega_i = \hat{T}_i/T_i$ for every two Blocks in each time period;

building, by the PET system, the true coincidence count loss correction model according to $\omega_i$ and the actual system single-photon count rate $S_i$.

8. A Positron Emission Tomography (PET) system, comprising:
a control device, comprising:
a processor, and
a non-transitory machine-readable storage medium storing machine executable instructions which are executable by the processor to:
obtain scanning data of a subject to be detected for which random correction has been performed, wherein the scanning data comprises a single-photon count rate of each of a plurality of Blocks in the PET system, a true coincidence count between every two of the plurality of the Blocks and a system single-photon count rate, where the system single-photon count rate is a sum of single-photon count rates of the plurality of the Blocks in the PET system;
determine a first correction factor corresponding to the true coincidence count according to the single-photon count rates of the two Blocks corresponding to the true coincidence count, wherein the first correction factor is used for correcting an effect of single-photon count losses for the two Blocks corresponding to the true coincidence count on the true coincidence count;
determine a second correction factor corresponding to the true coincidence count according to the system single-photon count rate, wherein the second correction factor is used for correcting an effect of the system single-photon count rate on the true coincidence count; and
correct the true coincidence count according to the first correction factor and the second correction factor corresponding to the true coincidence count.

9. The system of claim 8, wherein the processor is caused by the machine-executable instructions to:

obtain a single-photon count loss correction factor corresponding to each of the two Blocks according to the single-photon count rate of the Block corresponding to the true coincidence count;

determine the first correction factor corresponding to the true coincidence count according to single-photon count loss correction factors for the two Blocks corresponding to the true coincidence count.

10. The system of claim 9, wherein the processor is caused by the machine-executable instructions to:
multiply the single-photon count loss correction factors for the two Blocks to obtain the first correction factor corresponding to the true coincidence count.

11. The system of claim 9, wherein the processor is caused by the machine-executable instructions further to:
obtain a pre-built single-photon count loss correction model for the Block;
substitute the single-photon count rate of the Block into the single-photon count loss correction model for the block to obtain the single-photon count loss correction factor corresponding to the Block,
the processor is caused by the machine-executable instructions further to:
obtain a single-photon count loss correction factor $\eta_{ji}$ and a corresponding actual single-photon count rate $s_{ji}$ of each of the two Blocks in each of time periods when scanning a phantom injected with a radiopharmaceutical over the time periods;
build the single-photon count loss correction model for the block according to the single-photon count loss correction factor $\eta_{ji}$ and the actual single-photon count rate $s_{ji}$ of the Block in the time period.

12. The system of claim 8, wherein the processor is caused by the machine-executable instructions to:
obtain a pre-built true coincidence count loss correction model;
substitute the system single-photon count rate into the true coincidence count loss correction model to obtain the second correction factor corresponding to the true coincidence count,
the processor is caused by the machine-executable instructions further to:
determine an actual system single-photon count rate $S_i$, an actual true coincidence count rate between every two Blocks and an actual system true coincidence count rate $T_i$ in each time period i when scanning a phantom injected with a radiopharmaceutical over a plurality of time periods, obtaining, by the PET system, a single-photon count loss correction factor $\eta_{ji}$ for each Block j in the time period i;
multiply single-photon count loss correction factors for the two Blocks in the time period to obtain a product, multiplying, by the PET system, the obtained product by the actual true coincidence count rate for the two Blocks in the time period to obtain the true coincidence count rate for the two Blocks in the time period, wherein the effect of the single-photon count loss has been eliminated for the obtained true coincidence count rate;
obtain a sum of the true coincidence count rates for every two Blocks in each time period to obtain a system true coincidence count rate $T_i$ in each time period, wherein the effect of the single-photon count losses has been eliminated for the system true coincidence count rate $T_i$;
calculate a ratio $\alpha = [\Sigma(T_i/a_i)]/M$ or $\alpha = (\Sigma T_i)/(\Sigma a_i)$ of a theoretical true coincidence count rate to a pharmaceutical activity in a condition that there is no true coincidence count loss according to the actual system true coincidence count rate $T_i$ and the pharmaceutical activity $a_i$ in each of M time periods when there is no single-photon count loss;

calculate the theoretical true coincidence count rate $\hat{T}_i = \alpha a_i$ in each time period according to the ratio $\alpha$;

divide the theoretical true coincidence count rate $\hat{T}_i$ by $T_i$ to obtain a coincidence loss correction factor $\omega_i = \hat{T}_i/T_i$ for every two Blocks in each time period;

build the true coincidence count loss correction model according to $\omega_i$ and the actual system single-photon count rate $S_i$.

13. The system of claim 12, wherein the processor is caused by the machine-executable instructions to:

determine, by the PET system, a pharmaceutical activity $\alpha_i$ in each of time periods and an actual single-photon count rate $s_{ji}$ for each Block in each of the time periods when scanning a phantom injected with a pharmaceutical over the time periods, wherein i is a time period, and j is a Block;

calculate, by the PET system, a ratio $\lambda_j$ of a theoretical single-photon count rate of each of the Blocks to a pharmaceutical activity in a condition that there is no single-photon count loss according to the actual single-photon count rate $s_{ji}$ for the Block and the pharmaceutical activities $a_i$ in each of M time periods when there is no single-photon count loss, wherein $\lambda_j = [\Sigma(s_{ji}/\alpha_i)]/M$ or $\lambda_j = (\Sigma s_{ji})/(\Sigma \alpha_i)$;

calculate, by the PET system, the theoretical single-photon count rate $\bar{s}_{ji} = \lambda_j \alpha_i$ for each of the Blocks in each time period according to the ratio $\lambda_j$;

divide, by the PET system, $\bar{s}_{ji}$ by the actual single-photon count rate $s_{ji}$ to obtain the single-photon count loss correction factor $\eta_{ji} = \bar{s}_{ji}/s_{ji}$ for each of the Block in each time period.

14. The system of claim 8, wherein the processor is caused by the machine-executable instructions to:

multiply the first correction factor, the second correction factor, and the true coincidence count to obtain a product as a corrected true coincidence count.

* * * * *